(12) United States Patent
Lemer (10) Patent No.: US 12,372,667 B2
(45) Date of Patent: Jul. 29, 2025

(54) RADIATION PROTECTION SCREEN, FOR PROVIDING RADIATION PROTECTION OF AN OPERATOR AGAINST IONISING RADIATION

(71) Applicant: LEMER PAX, La Chapelle sur Erdre (FR)

(72) Inventor: Pierre-Marie Lemer, Nantes (FR)

(73) Assignee: LEMER PAX, La Chapelle sur Erdre (FR)

(*) Notice: Subject to any disclaimer, the term of this patent is extended or adjusted under 35 U.S.C. 154(b) by 165 days.

(21) Appl. No.: 18/025,597

(22) PCT Filed: Sep. 9, 2021

(86) PCT No.: PCT/EP2021/074851
§ 371 (c)(1),
(2) Date: Mar. 9, 2023

(87) PCT Pub. No.: WO2022/053575
PCT Pub. Date: Mar. 17, 2022

(65) Prior Publication Data
US 2023/0333265 A1   Oct. 19, 2023

(30) Foreign Application Priority Data

Sep. 10, 2020   (FR) .................................. 2009150

(51) Int. Cl.
*G01T 1/02* (2006.01)
*G21F 3/00* (2006.01)

(52) U.S. Cl.
CPC . *G01T 1/02* (2013.01); *G21F 3/00* (2013.01)

(58) Field of Classification Search
CPC .................................. G01T 1/02; G21F 3/00
See application file for complete search history.

(56) References Cited

U.S. PATENT DOCUMENTS

| 5,981,964 A | 11/1999 | McAuley et al. |
| 2013/0112897 A1 | 5/2013 | Eckhoff et al. |

FOREIGN PATENT DOCUMENTS

| CN | 204618263 U | * | 9/2015 |
| EP | 2 422 702 | | 2/2012 |
| JP | 2005253689 A | * | 9/2005 |

OTHER PUBLICATIONS

International Search Report dated Dec. 2, 2021, for PCT/EP2021/074851, 5 pp.

(Continued)

*Primary Examiner* — David P Porta
*Assistant Examiner* — Fani Polyzos Boosalis
(74) *Attorney, Agent, or Firm* — NIXON & VANDERHYE (57) ABSTRACT

Disclosed is a radiation shield, for providing radiation protection of an operator against ionizing radiation. This radiation protection screen is equipped with: —a first dosimetric measuring unit, for measuring an external radiation dose received on the side of the external face, —a second dosimetric measuring unit, for measuring an internal radiation dose received on the side of the internal face, —an electronic display, for displaying information intended for the operator; and —a controller, coupled with the dosimetric measuring unit and with the electronic display, for displaying, on the electronic display, information relating at least to the measured internal/external radiation doses.

16 Claims, 4 Drawing Sheets

(56) References Cited

OTHER PUBLICATIONS

Written Opinion of the ISA dated Dec. 2, 2021, for PCT/EP2021/074851, 5 pp.

* cited by examiner

RADIATION PROTECTION SCREEN, FOR PROVIDING RADIATION PROTECTION OF AN OPERATOR AGAINST IONISING RADIATION

CROSS-REFERENCE TO RELATED APPLICATIONS

This application is the U.S. national phase of International Application No. PCT/EP2021/074851 filed Sep. 9, 2021, which designated the U.S. and claims priority to FR 2009150 filed Sep. 10, 2020, the entire contents of each of which are hereby incorporated by reference.

TECHNICAL FIELD OF THE INVENTION

The present invention relates to the technical field of equipment for protection against ionising radiation.

More particularly, it relates to the radiation protection shields, enclosures and screens that are adapted for ensuring radiation protection of an operator against ionising radiation, advantageous in the medical field or other.

STATE OF THE ART

In some areas, the operators have to be able to protect themselves against exposure to ionising radiation, for example X or gamma rays.

This is in particular the case for the staff during certain interventions in the medical field, i.e. for example examinations of the catheterization type, implantation of a pacemaker, vascular, neurological or urological examinations.

The operator (technician, doctor, surgeon or other) then uses a structure for being protected against the radiation to which the patient is subjected.

Among the existing protective structures, the radiation protection screens are consisted of panels, or assembly of panels, made of radiation protection materials to ensure the radiation protection of the operator.

However, in practice, the operator often lacks concrete, objective and reliable data as regards the radiation protection efficiency of the screen behind which he intervenes.

But the present radiation protection screens have various and unequal qualities as regards their radiation protection efficiency.

There thus exists a need for a technical solution that would allow the operator to be informed, objectively and during intervention, about the protection efficiency provided by the radiation protection screen he uses.

SUMMARY OF THE INVENTION

In order to remedy the above-mentioned drawback of the state of the art, the present invention thus proposes a radiation protection screen that is adapted to ensure the radiation protection of an operator against ionising radiation.

The screen comprises a radiation protection wall made of a radiation protection material.

This radiation protection wall has two opposite faces:
an inner face, opposite which the operator is intended to position himself, and
an outer face, opposite which a source of ionising radiation has to be placed.

According to the invention, said radiation protection screen is fitted with:

first dosimetric measurement means, implanted opposite said outer face and adapted to measure an external radiation dose received on the side of said outer face,
second dosimetric measurement means, implanted opposite said inner face and adapted to measure an internal radiation dose received on the side of said inner face,
electronic display means, adapted to display information for the operator, and
control means, coupled to said dosimetric measurement means and said electronic display means.

The control means include a control module designed to display, on said electronic display means, information relating to at least said measured internal/external radiation doses.

In practice, the operator then has concrete, objective and reliable information/data as regards the radiation protection characteristics of the screen behind which he intervenes.

This technical solution allows the operator to know, objectively and directly, the protection efficiency provided by the radiation protection screen he uses during the intervention.

Other non-limiting and advantageous features of the product according to the invention, taken individually or according to all the technically possible combinations, are the following:

the control module is designed to display, on said electronic display means, at least chosen pieces of information among: a value of the internal radiation dose, a value of the external radiation dose, a differential radiation dose value (corresponding to the difference between said external radiation dose and said internal radiation dose), an attenuation value (corresponding to the ratio between said external radiation dose and said internal radiation dose), said values being advantageously in real time (also called "instantaneous values") and/or over a time period (also called "cumulative values"), and said values being advantageously expressed in equivalent dose;

the first measurement means are carried by the outer face of the radiation protection wall and the second measurement means are carried by the inner face of the radiation protection wall;

the electronic display means are carried by the inner face of the radiation protection wall and are arranged in such a way as to be visually accessible by the operator standing in front of said inner face;

the control means are coupled to said measurement means and/or to said electronic display means, by means of wired or wireless connection means;

the radiation protection screen comprises means for removable fastening of: said first dosimetric measurement means opposite the outer face of the radiation protection wall, and/or said second dosimetric measurement means opposite the inner face of the radiation protection wall, and/or the electronic display means opposite the inner face of the radiation protection wall;

the first dosimetric measurement means, and/or the second dosimetric measurement means, and/or the electronic display means, are each housed in a case removably fastened by magnetization to a metal wall of the screen;

the first dosimetric measurement means, and/or the second dosimetric measurement means, and/or the electronic display means, are each housed in a case removably fastened by insertion into a support housing fastened to the screen;

the first dosimetric measurement means, the second dosimetric measurement means, and the electronic display means are powered by batteries carried by the screen;

the first dosimetric measurement means, the second dosimetric measurement means and the electronic display means are each housed in a case integrating a battery for the powering thereof, said cases comprising a suitable connection system for recharging said batteries from a power source;

the screen comprises a radiation protection wall comprising a front panel extended by at least one lateral panel, said front and lateral panels extending over a height higher than the height of the operator in a standing position, the first dosimetric measurement means and the second dosimetric measurement means being fastened to said lateral panel, on an area located opposite the head part of said operator, and said electronic display means being fastened to said front panel;

the control means include an output for coupling to a remote computer;

the control means include a memory module, designed to record the information relating to the measured internal/external radiation doses;

the electronic display means and the control means consist of a one-piece electronic device.

The present invention also relates to a dosimetric device, for a radiation protection screen adapted to ensure the radiation protection of an operator against ionising radiation, said screen comprising a radiation protection wall made of a radiation protection material, said radiation protection wall comprising two opposite faces (an inner face, opposite which the operator has to stand, and an outer face, opposite which a source of ionising radiation has to be placed).

The dosimetric system comprises:

first dosimetric measurement means, intended to be implanted opposite said outer face and adapted to measure an external radiation dose received on the side of said outer face, second dosimetric measurement means, intended to be implanted opposite said inner face and adapted to measure an internal radiation dose received on the side of said inner face, electronic display means, adapted to display information for the operator, and control means, coupled to said dosimetric measurement means and said electronic display means, said control means including a control module designed to display, on said electronic display means, information relating to at least said measured internal/external radiation doses.

Obviously, the different features, alternatives and embodiments of the invention can be associated with each other according to various combinations, insofar as they are not incompatible or exclusive with respect to each other.

BRIEF DESCRIPTION OF THE DRAWINGS

Moreover, various other features of the invention emerge from the appended description made with reference to the drawings that illustrate non-limiting embodiments of the invention, and wherein.

DESCRIPTION OF THE PREFERRED EMBODIMENTS

It is to be noted that, in these figures, the structural and/or functional elements common to the different alternatives can have the same references numbers.

Figure 1:
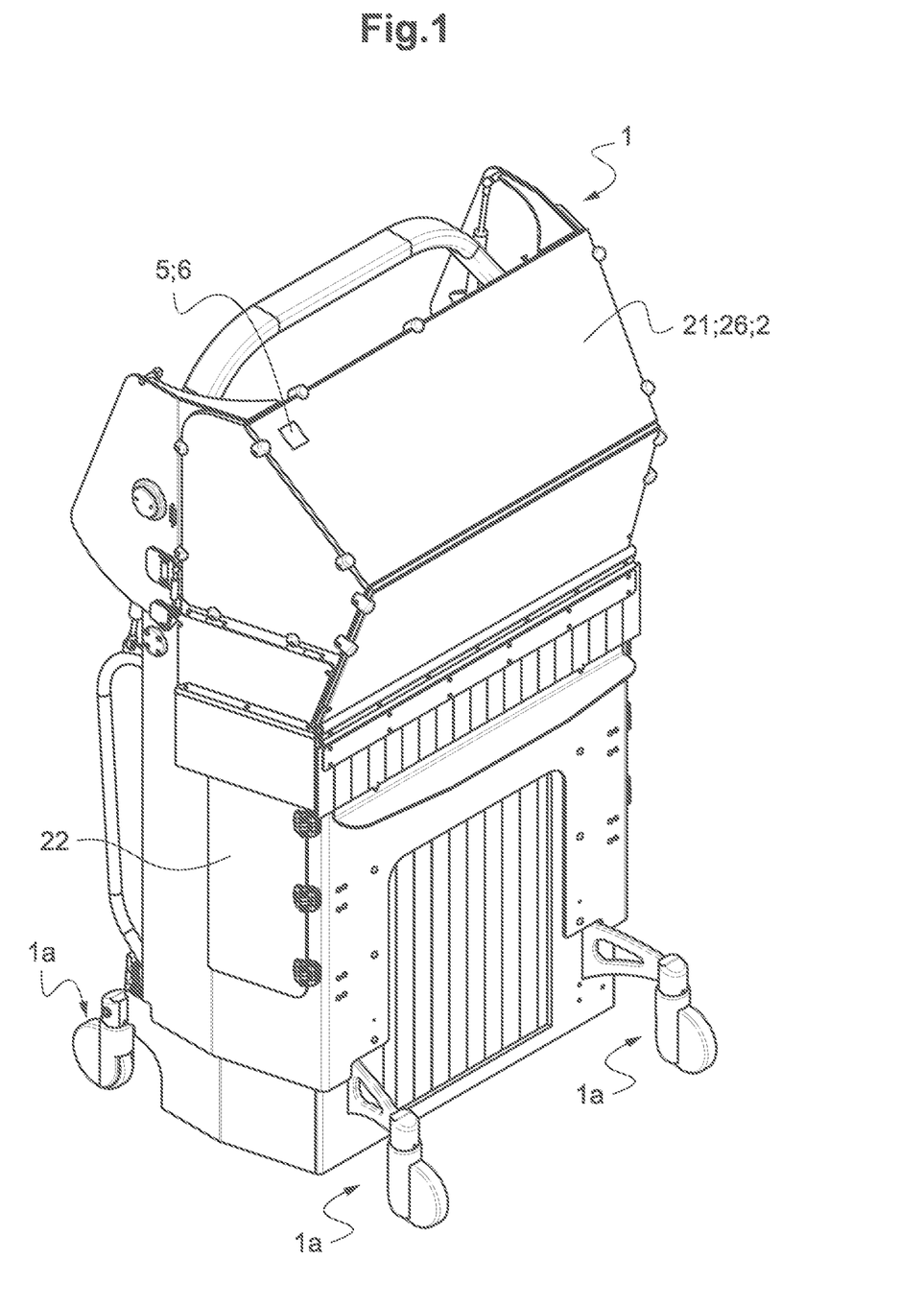
FIG. 1 is a general perspective view of a radiation protection screen according to the invention, fitted with the dosimetric system designed in particular to measure the internal/external radiation doses.
Figure 2:
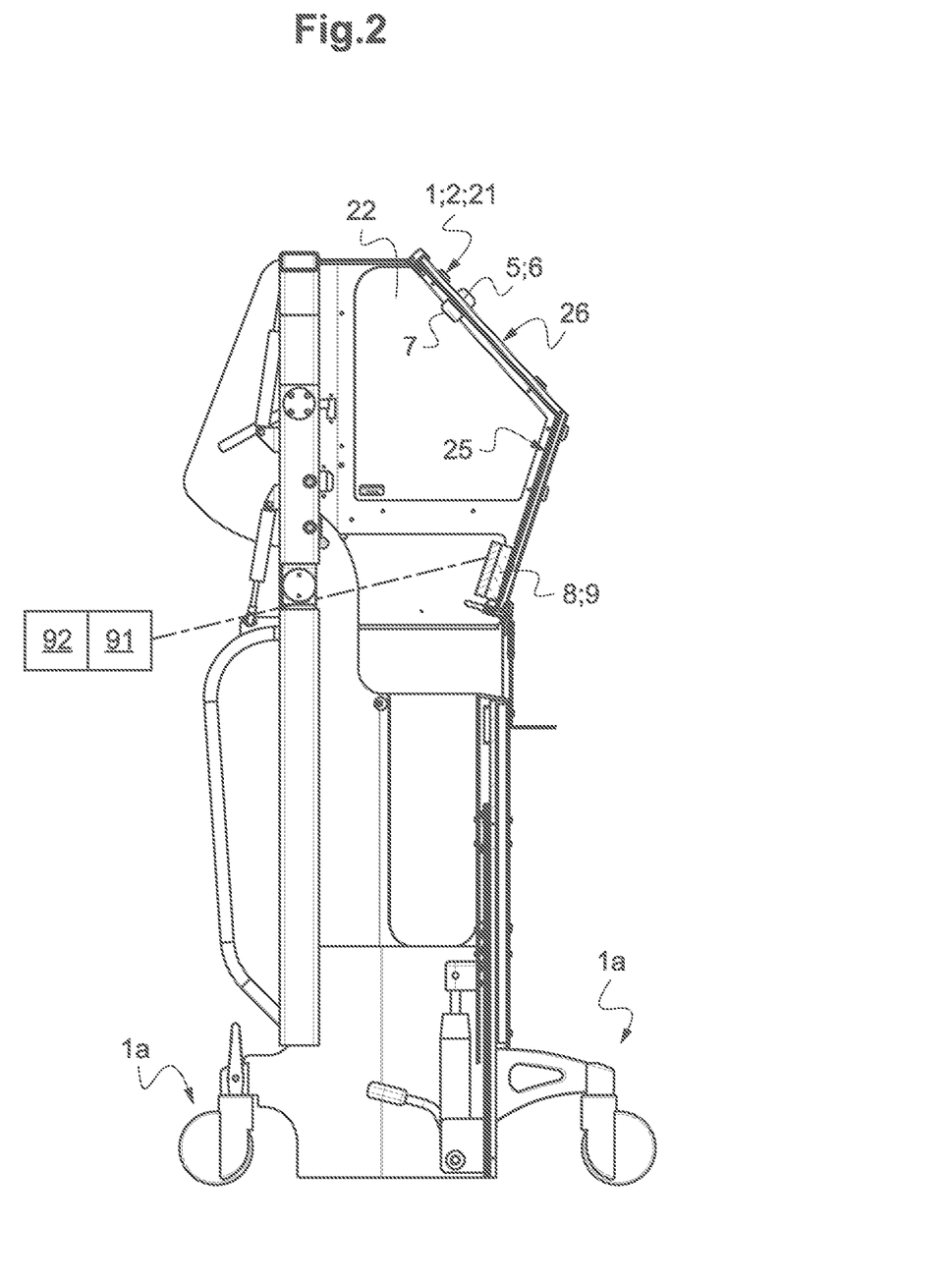
FIG. 2 is a general side view of the radiation protection screen according to FIG. 1, also illustrating the arrangement of the dosimetric system.
Figure 3:
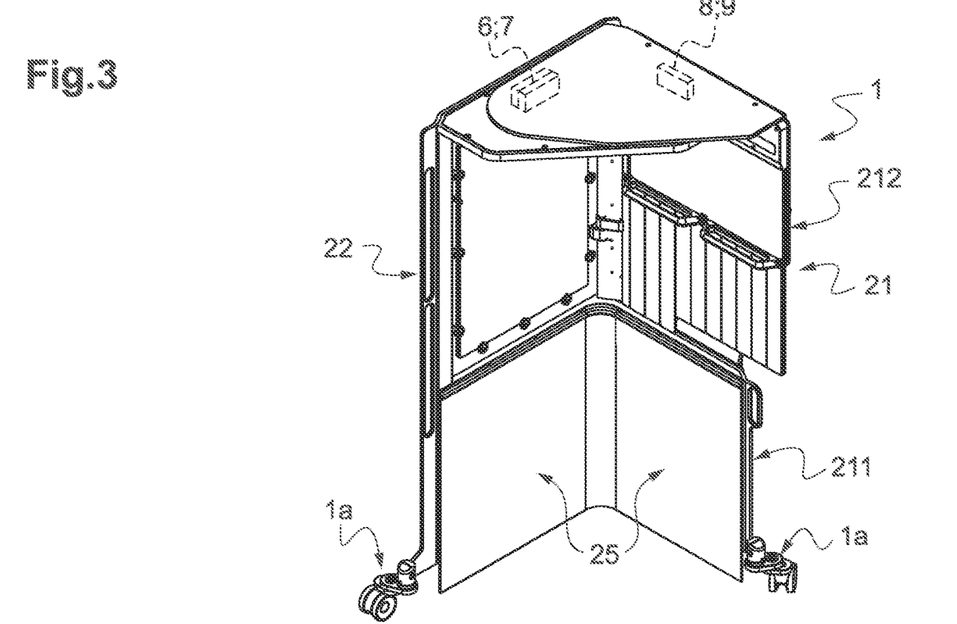
FIG. 3 is a general perspective view of an alternative embodiment of a radiation protection screen according to the invention.
Figure 4:
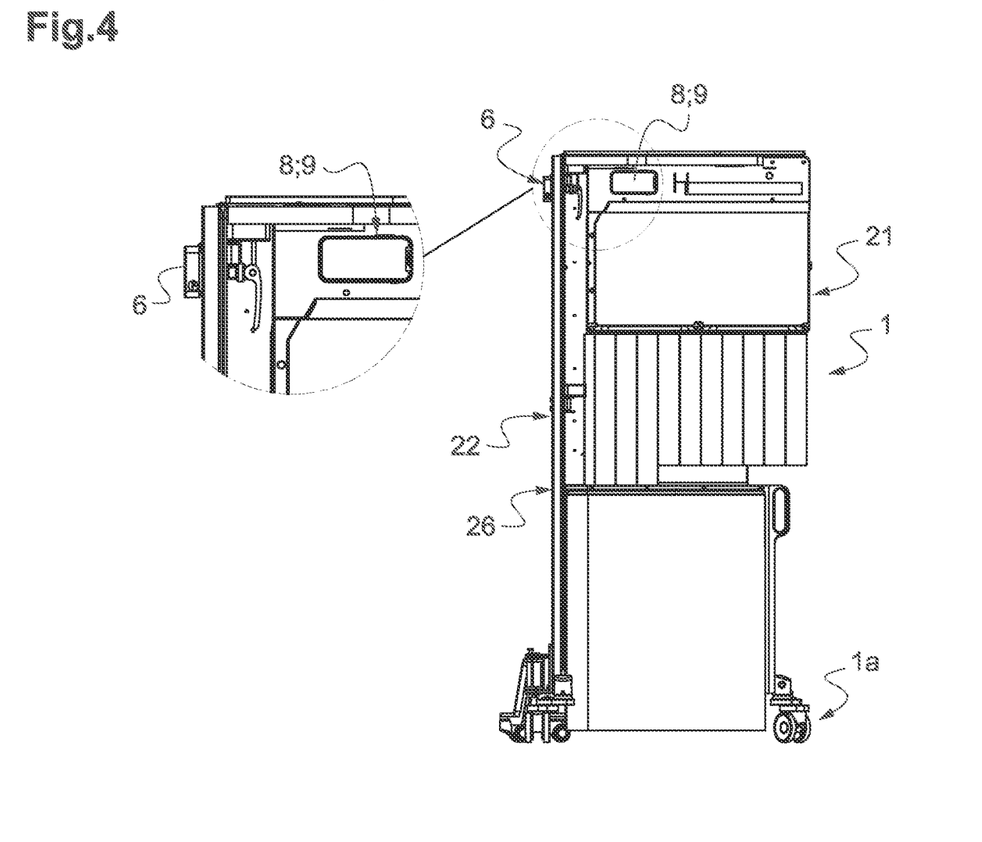
FIG. 4 is a front view of the radiation protection screen illustrated in FIG. 3, facing the inner face of its front panel.
Figure 5:
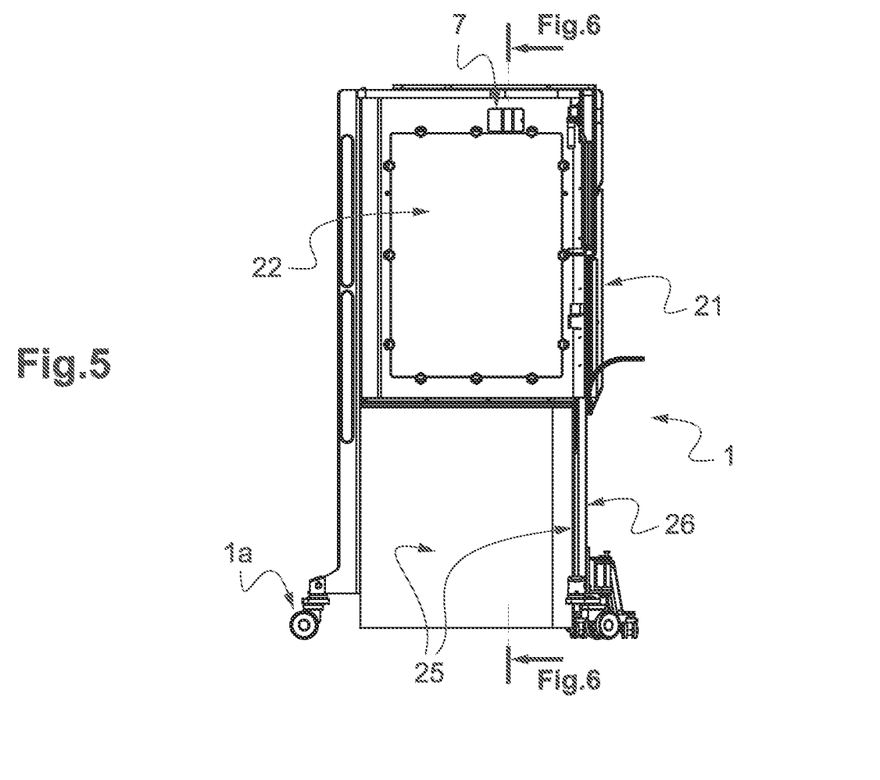
FIG. 5 is a front view of the radiation protection screen illustrated in FIG. 3, facing the inner face of its lateral panel.
Figure 6:
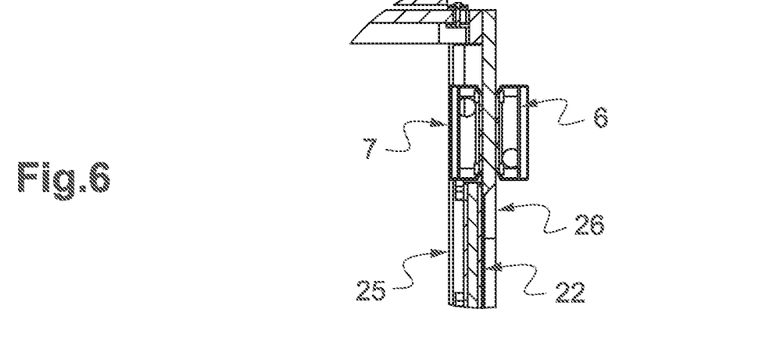
FIG. 6 is a cross-sectional view of the radiation protection screen according to the section plane 6-6 of FIG. 5.

The radiation protection screen 1 (also called "screen 1"), illustrated in FIGS. 1 and 2, is adapted to ensure the radiation protection of an operator against ionising radiation (for example, X or gamma rays).

Such a radiation protection screen 1 is advantageously used in the medical field, during certain interventions on patients, i.e. for example examinations of the catheterization type, implantation of a pacemaker, vascular, neurological or urological examinations.

The screen 1 is here in the form of a mobile cab with casters 1a for ground support to facilitate the movements thereof.

The operator (technician, doctor, surgeon or other) has to stand behind this radiation protection screen 1, in such a way as to be protected against the radiation to which the patient is subjected.

For that purpose, this screen 1 comprises a radiation protection wall 2 made of a radiation protection material.

This radiation protection material, conventional per se, is chosen for example among lead, steel, plastic material filled with radiation protection metal particles or also glass filled with radiation protection metal particles.

The radiation protection wall 2 is composed of a panel or an assembly of panels, extending generally vertically or at least approximately vertically over a height higher than the height of the operator in a standing position.

This radiation protection wall 2 advantageously comprises a front panel 21 that is possibly extended by at least one lateral panel 22 (herein by two lateral panels 22 each extending one of the sides of the front panel 21).

This radiation protection wall 2 has two opposite faces:

an inner face 25 (visible in FIG. 2), opposite which the operator has to stand, and an outer face 26, opposite which the source of ionising radiation has to be placed.

The screen 1 is thus intended to reduce, or even eliminate, the passage of the ionising radiation through the radiation protection wall 2. In other words, this screen 1 makes it possible to reduce, or even eliminate, the radiation dose from the outer face 26 to the inner face 25 of the radiation protection wall 2.

According to the present invention, this screen 1 is fitted with functional means that will provide the operator with concrete, objective and reliable data/information about the radiation protection efficiency.

These functional means are advantageously in the form of a dosimetric system 5 that comprises a combination of electronic components.

The radiation protection screen 1 is fitted, via the dosimetric system 5, with a couple of dosimetric measurement means:

first dosimetric measurement means 6, adapted to measure an external radiation dose Re received (or also "measured") on the side of said outer face 26, and second dosimetric measurement means 7, adapted to measure an internal radiation dose Ri received (or also "measured") on the side of said inner face 25.

In other words, the first dosimetric measurement means 6 are intended to be interposed between the source of ionising radiation and the screen 1, in such a way as to measure the external radiation dose Re received by the external face 26; the second dosimetric measurement means 7 are intended to be placed opposite the inner face 25, in such a way as to measure the radiation dose Ri that would be liable to pass through the screen 1.

By "radiation dose", it is advantageously understood the amount of energy communicated to an environment by an ionising radiation. This radiation dose is advantageously expressed in μSv or mSv or Gy (gray).

More precisely, the term "radiation dose" preferably encompasses the absorbed dose, the equivalent dose, the effective dose, the radioactive dose rate or the equivalent dose rate.

The absorbed dose is the amount of energy absorbed at a point per unit mass of material (inert or living). It is expressed in Grays (Gy) or in J/kg.

The equivalent dose is the product of the dose absorbed in a tissue or an organ by a weighting factor taking into account the biological effect linked to the radiation nature and energy. It is expressed in Sievert (Sv).

The efficient dose, also expressed in Sievert, corresponds to the sum of the weighted equivalent doses delivered by internal and external exposure to the different tissues and organs of the body.

The radioactive dose rate determines the radiation intensity (energy absorbed by the material by unit mass and time). It is measured in Gray per second (Gy/s).

The dose equivalent rate corresponds to the rate of absorbed dose quantity, weighted for biological effects by different quality factors according to the radiation. It is expressed in Sievert per second (Sv/s).

Herein, the first dosimetric measurement means 6 are implanted opposite the outer face 26. These first measurement means 6 are also preferably carried by this outer face 26 of the radiation protection wall 2.

The second dosimetric measurement means 7 are implanted opposite the inner face 25. Preferably, these second dosimetric measurement means 7 are carried by the inner face 25 of the radiation protection wall 2.

Preferably, these first dosimetric measurement means 6 and/or the second dosimetric measurement means 7 are each integrated in a support case that is removable fastened to the screen 1 or removably carried by the screen 1. The corresponding cases may for example be fastened by magnetization to a metal part of the screen 1 frame; as an alternative, they may be put into suitable receiving housings/receptacles, themselves removably fastened to the screen 1.

The first dosimetric measurement means 6 and the second dosimetric measurement means 7 are advantageously implanted at a height, with respect to the ground, from 1,500 to 1,900, preferably from 1,600 to 1,800 mm (advantageously corresponding to a height of the head, in particular the eyes or also the temporal lobe, of the operator who is located on the radioactive source side).

The first dosimetric measurement means 6 and the second dosimetric measurement means 7 may be arranged opposite (i.e. facing) each other and sandwich the radiation protection wall 2; as an alternative, the first dosimetric measurement means 6 and the second dosimetric measurement means 7 may be staggered relative to each other.

These first dosimetric measurement means 6 and second dosimetric measurement means 7 may be implanted on one of the sides of the front panel 21 (as illustrated in FIGS. 1 and 2), or on one of the lateral panels 22 (in particular on the lateral panel intended to be located on the radioactive source side).

To measure such radiation doses, the dosimetric measurement means 6, 7 advantageously consist of at least two individual electronic devices that are each adapted to measure/determine an external exposure to the ionising radiation of the received dose for the whole body.

Such dosimetric measurement means 6, 7 are advantageously chosen among the dosimeters conventional per se, preferably the electronic dosimeters.

These dosimeters preferably consist of operational or active dosimeters, capable of measuring/collecting the radiation dose received in real time.

They may be of the Geiger-Muller radiation counter type.

The support cases of the first and second dosimetric measurement means 6, 7 advantageously integrate a battery to ensure energy autonomy. And the cases in question comprise a suitable connection system for recharging the battery from a power source. This recharging operation is facilitated by the removable mounting of the cases on the screen 1.

For implementation of these dosimetric measurement means 6, 7, as illustrated in FIG. 2, the radiation protection screen 1 is also fitted with:

electronic display means 8, adapted to display information/data for the operator, and control means 9, coupled to the dosimetric measurement means 6, 7 (to process the data collected) and to the electronic display means 8 (to control the information provided to the operator).

The electronic display means 8 and the control means 9 are advantageously housed in a same support case that advantageously integrates a battery, to ensure energy autonomy.

Here again, the corresponding case comprises a suitable connection system for recharging the battery from a power source.

According to an alternative embodiment, the screen 1 may comprise a rechargeable battery suitable to power the dosimetric measurement means 6, 7, the electronic display means 8 and the control means 9 by means of a wired network.

Preferably, the electronic display means 8, with possibly the control means 9, are carried by the inner face 25 of the radiation protection wall 2. Their support case may be removably carried by the screen 1 by magnetization or by integration in a support housing/receptacle; this removable mounting of the case on the screen 1 facilitates the recharging operation of the integrated battery.

They are further arranged in such a way as to be visually accessible by the operator positioned in front of this inner face 25 during the intervention.

Such electronic display means 8 are advantageously in the form of an output peripheral device, for example a display screen (or monitor).

The control means 9 advantageously consist of a computing/electronic unit, for example a computer, which comprises:
- a processing unit, also called "computing unit" or "processor", and
- data storage means containing a database and at least one computer program.

The connection of the control means 9 with, on the one hand, the dosimetric measurement means 6, 7 and, on the other hand, the electronic display means 8, is preferably implemented using wireless connection means (Wifi, Bluetooth, ZigBee, etc.), not shown. As an alternative, this connection may be a wired connection.

According to a preferred embodiment, the electronic display means 8 and the control means 9 consist of a one-piece electronic device (common case), for example of the tablet type, possible a touch tablet.

In the case of wireless connection means, the dosimetric measurement means 6, 7 are advantageously respectively fitted with a wireless transceiver communication module.

The control means 9 include a control module 91 designed to display, on the electronic display means 8, information/data relating to at least the measured internal –Ri/external –Re radiation doses.

Such a control module 91 is preferably chosen among the computer programs comprising instructions that, when the program is executed by a computer, cause said computer to display, on the electronic display means 8, information/data relating to at least the measured internal –Ri/external –Re radiation doses.

The term "information/data relating to at least the measured internal Ri/external Re radiation doses" advantageously encompasses:
- the values of the measured internal Ri/external Re radiation doses, as such, displayed directly after their respective measurements, and/or
- values derived from these measured internal Ri/external Re radiation doses, resulting from a processing by this same control module 91.

Preferably, the control module 91 is designed to display, on the electronic display means 8, at least information chosen among:
- the value Ri of the internal radiation dose, collected by the second dosimetric measurement means 7 (implanted opposite said internal face 25),
- the value Re of the external radiation dose, collected by the first dosimetric measurement means 6 (implanted opposite said external face 26),
- a differential radiation dose value, corresponding to the difference between said external radiation dose Re and said internal radiation dose Ri,
- an attenuation coefficient value of the screen 1,
- an attenuation value, corresponding to the ratio between said external radiation dose (Re) and said internal radiation dose (Ri), advantageously expressed in percentage of said external radiation dose (Re).

The values displayed on the electronic display means 8 advantageously comprise:
- real time or instantaneous values ("real time" mode), and/or
- values over a time period or cumulative values ("monitoring" mode), for example for the time of an examination or an intervention, interesting in particular for the dosimetric monitoring.

The cumulative value may be individualized for a given user, with a user recognition means (badge, etc.).

These displayed values are advantageously expressed in equivalent dose.

The control means 9 comprise a memory module 92, designed to record the information/data relating to the measured internal Ri/external radiation Re doses.

Such a memory module 92 is preferably chosen among the computer programs comprising instructions that, when the program is executed by a computer, cause said computer to record into the data storage means the information/data relating to at least the measured internal Ri/external Re radiation doses.

The control means 9 may also comprise an output (not shown), for example in the form of a computer bus (for example, an USB port), to connect a computer peripheral device.

This coupling of the control means 9, wired or wireless, is advantageously carried out with a remote computer, for example in the form of a server.

This output is useful for the exchange of data (in particular, the information relating to the measured internal Ri/external Re radiation doses) with the remote computer in the context of a dosimetric monitoring.

Generally, the radiation protection screen 1 is fitted with the dosimetric system 5, from the outset or added to posteriori.

In an "added" configuration, the dosimetric system 5 advantageously consists of an "autonomous" device that is adapted to be added to an existing radiation protection screen 1 for the improvement/updating of the latter.

Still generally, the different components of the dosimetric system 5 are carried by the radiation protection screen 1, through assembly means (possibly via dedicated support elements).

In operation, the radiation protection screen 1 is interposed between the operator and the ionising radiation source.

The operator is then positioned behind the screen 1 opposite its inner face 25.

During the intervention, the dosimetric system 5 collects the internal Ri/external Re radiation doses.

The dosimetric system 5 also ensures the processing of the data collected through the control means 9, and provides the data relating to at least the internal Ri/external Re radiation doses via the electronic display means 8.

All along the intervention, the operator can thus visualize the concrete, objective and reliable data, in "real time" mode and/or "monitoring" mode, as regards the radiation protection efficiency of the radiation protection screen 1.

FIGS. 3 to 6 illustrate an alternative embodiment of a screen 1 according to the invention, as a mobile cab mounted on casters 1a.

Here again, this screen 1 comprises a radiation protection wall 2 made of a radiation protection material.

This radiation protection material, conventional per se, is chosen for example among lead, steel, plastic material filled with radiation protection metal particles or also glass filled with radiation protection metal particles.

The radiation protection wall 2 is composed of a panel and an assembly of panels, extending generally vertically or at least approximately vertically over a height higher than the height of the operator in a standing position.

This radiation protection wall 2 here comprises a front panel 21 that is extended on one of its sides by a lateral panel 22. The front panel 21 comprises:
- a lower part 211, fixed with respect to the lateral panel 22 and extending according to an angle of the order of 90°, with respect to the latter, and a movable, upper part 212, mounted swivelling about a vertical axis on the side opposite the lateral panel 22.

The radiation protection wall 2, formed of the front panel 21 and the lateral panel 22, comprises two opposite faces:
- an inner face 25, opposite which the operator has to stand, and
- an outer face 26, opposite which the source of ionising radiation has to be placed.

As for the embodiment, illustrated in FIGS. 1 and 2, the screen 1 illustrated in FIGS. 3 to 6 comprises:
- first dosimetric measurement means 6, adapted to measure an external radiation dose Re received (also said "measured") on the side of the outer face 26,
- second dosimetric measurement means 7, adapted to measure an internal radiation dose Ri received (also said "measured") on the side of the inner face 25,
- electronic display means 8, adapted to display information/data for the operator, and
- control means 9, coupled to the dosimetric measurement means 6, 7 (to process the data collected) and to the electronic display means 8 (to control the information provided to the operator).

The first dosimetric measurement means 6 and the second dosimetric measurement means 7 are here arranged opposite each other (that is to say facing each other) in the upper part of the lateral panel 22, in an area located near the head of the operator, and more particularly opposite the temporal lobe of the operator who is located on the radioactive source side.

Preferably, these first dosimetric measurement means 6 and the second dosimetric measurement means 7 are each integrated in a support case that is removable fastened to or removably carried by the screen 1. The corresponding cases may for example be fastened by magnetization to a metal part of the screen frame; as an alternative, they may be put into suitable receiving housings/receptacles, themselves removably fastened to the screen 1.

The support cases of the first and second dosimetric measurement means 6, 7 advantageously integrate a battery to ensure energy autonomy. And the cases in question comprise a suitable connection system for recharging the batteries from a power source. This recharging operation is facilitated by the removable mounting of the cases on the screen 1 (the cases may thus be detached from the screen to be connected to a suitable battery charger).

The electronic display means 8 and the control means 9 are housed in a same support case fastened in the upper part of the front panel 21, on the inner face 25 side of the screen 1.

This support case is advantageously removably carried by the screen 1 by magnetization or by integration into a support housing.

This support case advantageously integrates a battery, to ensure energy autonomy; and it comprises a suitable connection system for recharging said battery from a power source. This recharging operation is facilitated by the removable mounting of the case on the screen 1.

The control of the electronic display means 8 by the control means 9 based on the information received from the dosimetric measurement means 6 and 7 is made as described hereinabove in relation with the embodiment of FIGS. 1 and 2.

Figure 7:
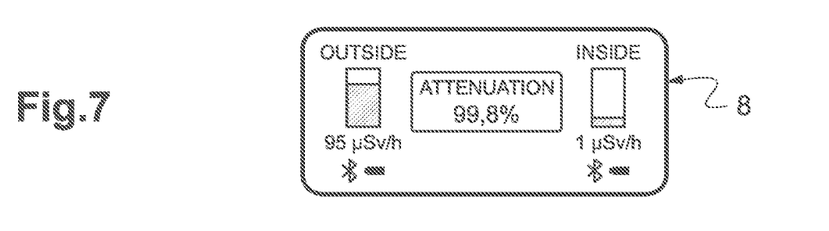
FIG. 7 illustrates a possible example of the information liable to be provided by the electronic display means of the radiation protection screen according to the invention.

FIG. 7 illustrates a possible example of the information liable to be provided by the electronic display means 8.

The external radiation dose Re detected by the first dosimetric measurement means 6 here appears on the left of the screen. The internal radiation dose Ri detected by the second dosimetric measurement means 7 appears on the right of the screen; and the radiation attenuation value is displayed in the central part.

The screen may also display other pieces of information, for example relating to the battery charge of the dosimetric measurement means 6 and 7, and to the correct operation of the wireless connection.

The invention claimed is:

1. A radiation protection screen, that is adapted to ensure the radiation protection of an operator against ionizing radiation,
    said screen comprising a radiation protection wall made of a radiation protection material,
    said radiation protection wall having two opposite faces:
        an inner face, opposite which the operator is intended to position himself, and
        an outer face, opposite which a source of ionizing radiation has to be placed,
    wherein said radiation protection screen is fitted with:
        first dosimetric measurement means, implanted opposite said outer face and adapted to measure an external radiation dose received on the side of said outer face,
        second dosimetric measurement means, implanted opposite said inner face and adapted to measure an internal radiation dose received on the side of said outer face,
        electronic display means, adapted to display information for the operator, and
        control means, coupled to said dosimetric measurement means and said electronic display means,
    said control means including a control module designed to display, on said electronic display means, information relating to at least said measured internal/external radiation doses.

2. The radiation protection screen according to claim 1, wherein the control module is designed to display, on said electronic display means, at least information chosen among:
    a value of the internal radiation dose,
    a value of the external radiation dose,
    a differential radiation dose value, corresponding to the difference between said external radiation dose and said internal radiation dose, and
    an attenuation value, corresponding to the ratio between said external radiation dose and said internal radiation dose.

3. The radiation protection screen according to claim 1, wherein the first dosimetric measurement means are carried by the outer face of the radiation protection wall and the second measurement means are carried by the inner face of the radiation protection wall.

4. The radiation protection screen according to claim 1, wherein the electronic display means are carried by the inner face of the radiation protection wall and are arranged in such a way as to be visually accessible by the operator standing in front of said inner face.

5. The radiation protection screen according to claim 1, wherein the control means are coupled to said dosimetric measurement means and/or to said electronic display means by means of wired or wireless connection means.

6. The radiation protection screen according to claim 1, further comprising means for the removable fastening of:
    said first dosimetric measurement means opposite the outer face of the radiation protection wall, and/or
    said second dosimetric measurement means opposite the inner face of the radiation protection wall, and/or the electronic display means opposite the inner face of the radiation protection wall.

7. The radiation protection screen according to claim 6, wherein said first dosimetric measurement means, and/or said second dosimetric measurement means, and/or said electronic display means, are each housed in a case removably fastened by magnetization to a metal wall of said screen.

8. The radiation protection screen according to claim 6, wherein said first dosimetric measurement means, and/or said second dosimetric measurement means, and/or said electronic display means, are housed in a case removably fastened by insertion into a support housing fastened to said screen.

9. The radiation protection screen according to claim 1, wherein said first dosimetric measurement means, said second dosimetric measurement means and said electronic display means are powered by batteries carried by said screen.

10. The radiation protection screen according to claim 9, wherein said first dosimetric measurement means, said second dosimetric measurement means and said electronic display means are each housed in a case integrating a battery for the powering thereof, said cases comprising a suitable connection system for recharging said batteries from a power source.

11. The radiation protection screen according to claim 1, further comprising a radiation protection wall comprising a front panel extended by at least one lateral panel, said front and lateral panels extend over a height higher than the height of said operator in a standing position,
said first dosimetric measurement means and said second dosimetric measurement means being fastened to said lateral panel, on an area located opposite the head part of said operator,
and said electronic display means being fastened on said front panel.

12. The radiation protection screen according to claim 1, wherein the control means includes an output for coupling to a remote computer.

13. The radiation protection screen according to claim 1, wherein the control means includes a memory module designed to record the information relating to the measured internal/external radiation doses.

14. The radiation protection screen according to claim 1, wherein the electronic display means and the control means consist of a single-piece electronic device.

15. The radiation protection screen according to claim 1, wherein the first dosimetric measurement means are carried by the outer face of the radiation protection wall and the second measurement means are carried by the inner face of the radiation protection wall, and
wherein the electronic display means are carried by the inner face of the radiation protection wall and are arranged in such a way as to be visually accessible by the operator standing in front of said inner face;
wherein the radiation protection screen comprises a radiation protection wall comprising a front panel that extends over a height higher than the height of the operator in a standing position, said first dosimetric measurement means and said second dosimetric measurement means being fastened on an area located opposite the head part of said operator;
the radiation protection screen further comprising a radiation protection wall comprising a front panel extended by at least one lateral panel, said front and lateral panels extend over a height higher than the height of said operator in a standing position,
said first dosimetric measurement means and said second dosimetric measurement means being fastened to said lateral panel, on an area located opposite the head part of said operator, and
said electronic display means being fastened on said front panel.

16. A dosimetric system, for a radiation protection screen for providing radiation protection of an operator against ionizing radiation,
said screen comprising a radiation protection wall made of a radiation protection material,
said radiation protection wall comprising two opposite faces: an inner face, opposite which the operator has to stand, and an outer face, opposite which a source of ionizing radiation has to be placed,
said dosimetric system comprising:
first dosimetric measurement means, intended to be implanted opposite said outer face and adapted to measure an external radiation dose received on the side of said outer face,
second dosimetric measurement means, intended be implanted opposite said inner face and adapted to measure an internal radiation dose received on the side of said inner face,
electronic display means, adapted to display information for the operator, and
control means, coupled to said dosimetric measurement means and said electronic display means,
said control means including a control module designed to display, on said electronic display means, information relating to at least said measured internal/external radiation doses.

* * * * *